(12) United States Patent
Giaretta

(10) Patent No.: US 11,957,244 B2
(45) Date of Patent: Apr. 16, 2024

(54) CHEST OF DRAWERS

(71) Applicant: Dental Art S.P.A., Montecchio Precalcino (IT)

(72) Inventor: Fabio Giaretta, Montecchio Precalcino (IT)

(73) Assignee: Dental Art S.P.A., Montecchio Precalcino (IT)

( * ) Notice: Subject to any disclaimer, the term of this patent is extended or adjusted under 35 U.S.C. 154(b) by 39 days.

(21) Appl. No.: 17/800,473

(22) PCT Filed: Feb. 23, 2021

(86) PCT No.: PCT/IB2021/051499
§ 371 (c)(1),
(2) Date: Aug. 17, 2022

(87) PCT Pub. No.: WO2021/171169
PCT Pub. Date: Sep. 2, 2021

(65) Prior Publication Data
US 2023/0070898 A1      Mar. 9, 2023

(30) Foreign Application Priority Data

Feb. 27, 2020      (IT) .................. 102020000004039

(51) Int. Cl.
*A47B 67/04*      (2006.01)
*A61B 50/20*      (2016.01)
(Continued)

(52) U.S. Cl.
CPC .............. *A47B 67/04* (2013.01); *A61B 50/20* (2016.02); *A61G 15/16* (2013.01); *A47B 88/944* (2017.01);
(Continued)

(58) Field of Classification Search
CPC ....... A47B 67/04; A47B 88/944; A61B 50/20; A61B 2050/185; A61B 2050/3008; A61G 15/16

See application file for complete search history.

(56) References Cited

U.S. PATENT DOCUMENTS 1,466,335 A  *  8/1923  Gleason  ............... A47B 88/906
                                                          211/49.1
3,942,851 A  *  3/1976  Kaplan  ................. A47F 5/0037
                                                          312/328
(Continued)

FOREIGN PATENT DOCUMENTS

CN          107 007 041 A        8/2017

OTHER PUBLICATIONS

Ajn, Color Cording to Reduce Errors, Jan. 1, 2005, XP055533105, retrieved http://pedied.com/documents/Articles/DeBoer-Broselow%20article%20ajn.pdf., pp. 1-70.
(Continued)

*Primary Examiner* — James O Hansen
(74) *Attorney, Agent, or Firm* — Workman Nydegger

(57) ABSTRACT

Chest of drawers includes a fixed structure which defines at least one housing configured to house at least one moveable drawer configured to have a closed position with respect to the fixed structure in which the drawer is completely contained inside the housing and an open position in which at least part of the drawer protrudes outside the housing. The chest of drawers includes a first identification element visible from the outside of the fixed structure configured to provide information regarding the contents of the drawer.

11 Claims, 4 Drawing Sheets

(51) Int. Cl.
  *A61G 15/16* (2006.01)
  *A47B 88/944* (2017.01)
  *A61B 50/18* (2016.01)
  *A61B 50/30* (2016.01)

(52) U.S. Cl.
  CPC . *A61B 2050/185* (2016.02); *A61B 2050/3008* (2016.02)

(56) References Cited

U.S. PATENT DOCUMENTS

| | | | | |
|---|---|---|---|---|
| 4,413,867 | A * | 11/1983 | Mosebrook | A47B 87/02 206/509 |
| 5,137,340 | A * | 8/1992 | Cugley | A47B 87/02 312/234.5 |
| 8,430,461 | B1 * | 4/2013 | Cole | A47B 81/005 312/204 |
| 2004/0232809 | A1 * | 11/2004 | Buchman-Ziv | B44C 3/12 312/293.2 |
| 2012/0319550 | A1 * | 12/2012 | Manniso | A47B 88/994 312/348.3 |
| 2013/0270984 | A1 * | 10/2013 | Chuda | A47B 67/04 312/348.3 |
| 2015/0091422 | A1 | 4/2015 | Alder et al. | |
| 2019/0201571 | A1 | 7/2019 | Lucier et al. | |

OTHER PUBLICATIONS

International Search Report and Written Opinion dated Jun. 8, 2021, issued in PCT Application No. PCT/IB2021/051499, filed Feb. 23, 2021.

* cited by examiner

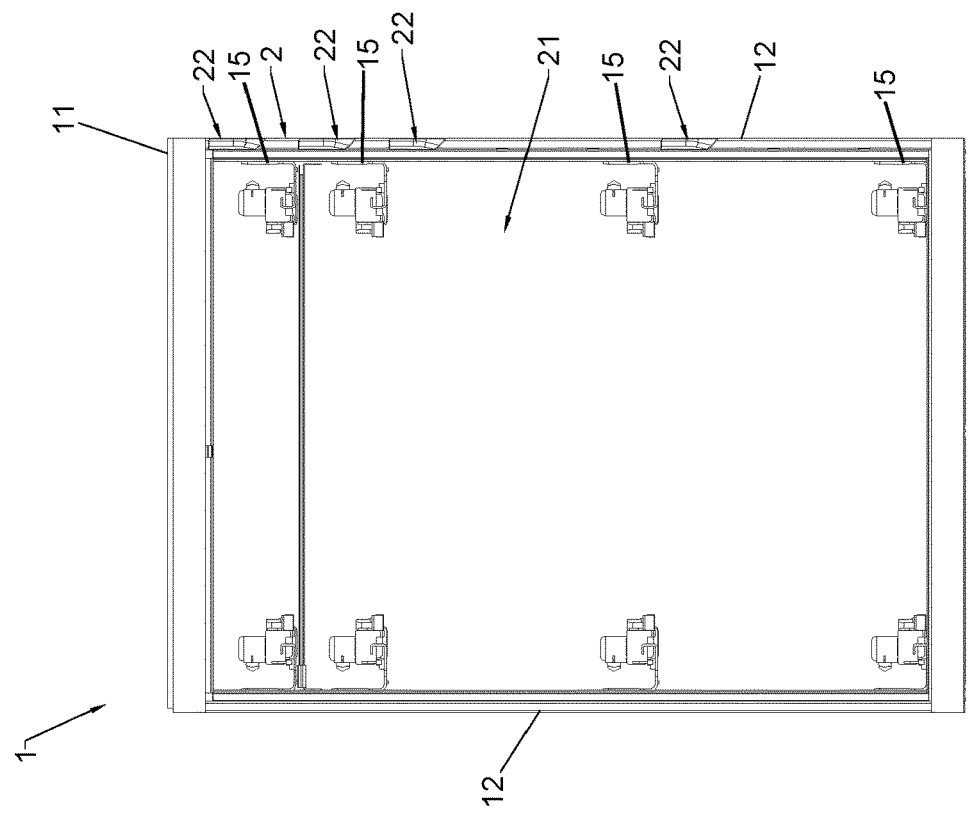
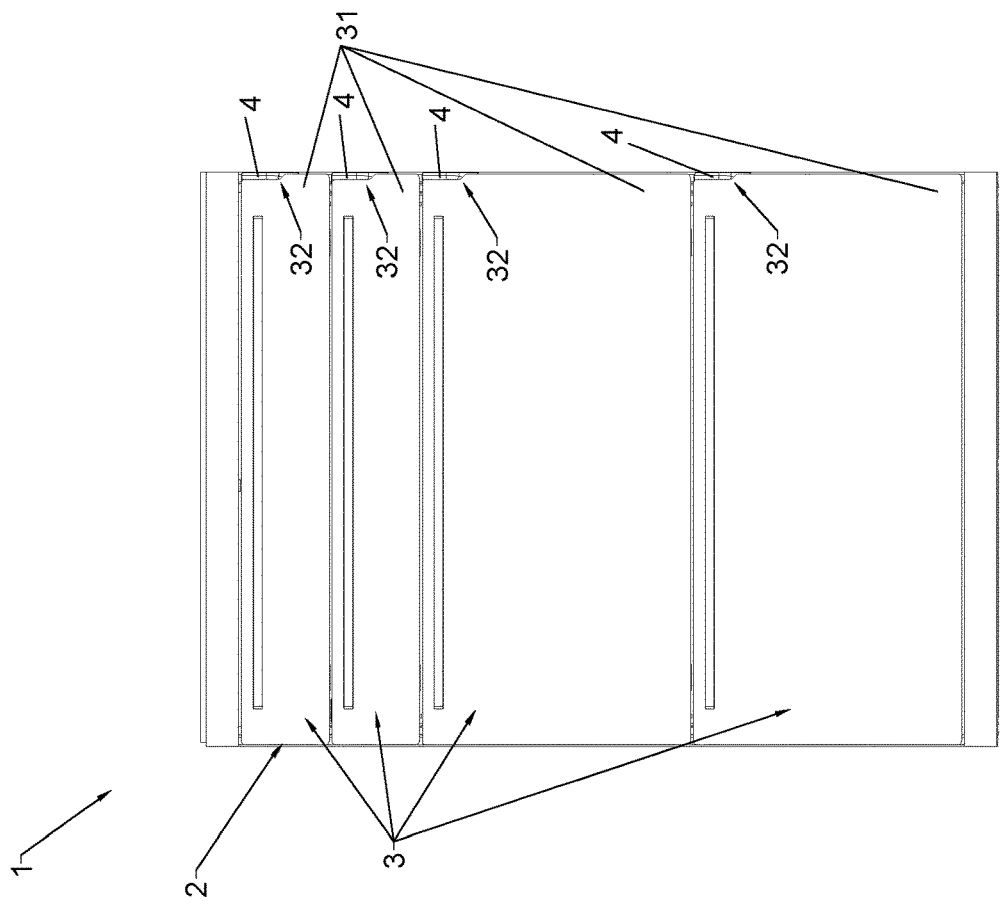
Fig.1
Fig.2

CHEST OF DRAWERS

BACKGROUND OF THE INVENTION

1. The Field of the Invention

The present invention relates to an improved chest of drawers, particularly a chest of drawers suitable for use in medical-surgical facilities such as, for example, dental practices.

2. The Relevant Technology

Medical-surgical offices, as well as dental practices in particular, are controlled environments, equipped with specific types of furniture and a plurality of devices that enable doctors and medical personnel to perform treatments on patients.

As far as dental practices are concerned, the fulcrum of the devices and furnishings is represented by the so-called "dental unit".

The unit essentially comprises a chair with a reclining backrest, on which the patient sits, and around which the dentist and his assistant are positioned on opposite sides.

The "dental delivery system", which is a movable assembly belonging to the dental unit, where several dental instruments, such as handpieces, dental turbines and air water syringes are arranged, is positioned on the side where the dentist is located.

On the same side there is also a table, called a tray stand, for trays containing tools and/or other materials to be used during dental interventions, such as dental burs for turnines, photopolymerization lamps, resins for fillings, etc.

In particular, the tools or materials that may be used during the interventions are numerous and have very different characteristics.

The tools or materials used by the dentist, in fact, must be suitable for many types of interventions and different types of patients.

These numerous instruments, properly cleaned and sterilized, are placed inside drawers neatly arranged in chests of drawers and removed as needed.

In a dental practice, furthermore, these chests of drawers are generally arranged at a distance from the dental unit such that they can be quickly reached by the dentist or assistant to take the required instruments when needed.

Given that there are a number of them, these tools are usually subdivided by category within the drawers. It is therefore important for healthcare professionals to memorize the contents of each drawer in order to speed up the instrument retrieval procedure which is usually carried out while the patient is undergoing a treatment.

If the healthcare professional does not know the contents of the individual drawers of the chest of drawers in advance, he will have to disadvantageously attempt to find the needed tool by opening the drawers one after another until he finds what he needs.

One possible solution to remediate this drawback is represented by the use of adhesive labels placed on the front of each drawer indicating the contents thereof.

Disadvantageously, adhesive labels are subject to deterioration, detachment or discoloration over time, so it is often necessary to remove and replace them, with a consequent waste of time.

Also disadvantageously, the removal and replacement must also be carried out if the contents of the drawer must be changed, or if new items that were not indicated on the label are placed in the drawer.

Document CN1007007041 discloses a fixed structure whose outer walls and doors define a housing. Inside this housing there are hosted a drawer and also identification elements.

SUMMARY OF THE INVENTION

The present invention aims to overcome all the limitations and drawbacks indicated.

In particular, one object of the present invention is to provide a chest of drawers and a method which enable the contents of each drawer located therein to be identified quickly.

It is a further object of the present invention that the identification method be adaptable according to requirements.

Still another object of the present invention is that the chest of drawers and the method enable the identification of the contents of each drawer without having to open it.

The aforementioned aims are achieved with a chest of drawers, in particular a chest of drawers for dental practices, in accordance with the main claim.

Further characteristics of the chest of drawers are described in the dependent claims.

The objects are also achieved through the method for identifying the contents of a drawer in a chest of drawers, as indicated in the claims.

BRIEF DESCRIPTION OF THE DRAWINGS

The aforementioned objects, together with the advantages to be explained hereinafter, will be highlighted in the description of a preferred embodiment of the invention which is provided, by way of a non-limiting example, with reference to the attached drawings, where:

FIG. 1 shows a front view of an embodiment of the chest of drawers of the invention according to a first embodiment;

FIG. 2 shows a front view of the chest of drawers of FIG. 1 without the drawers;

DETAILED DESCRIPTION OF THE PREFERRED EMBODIMENTS

Figure 4:
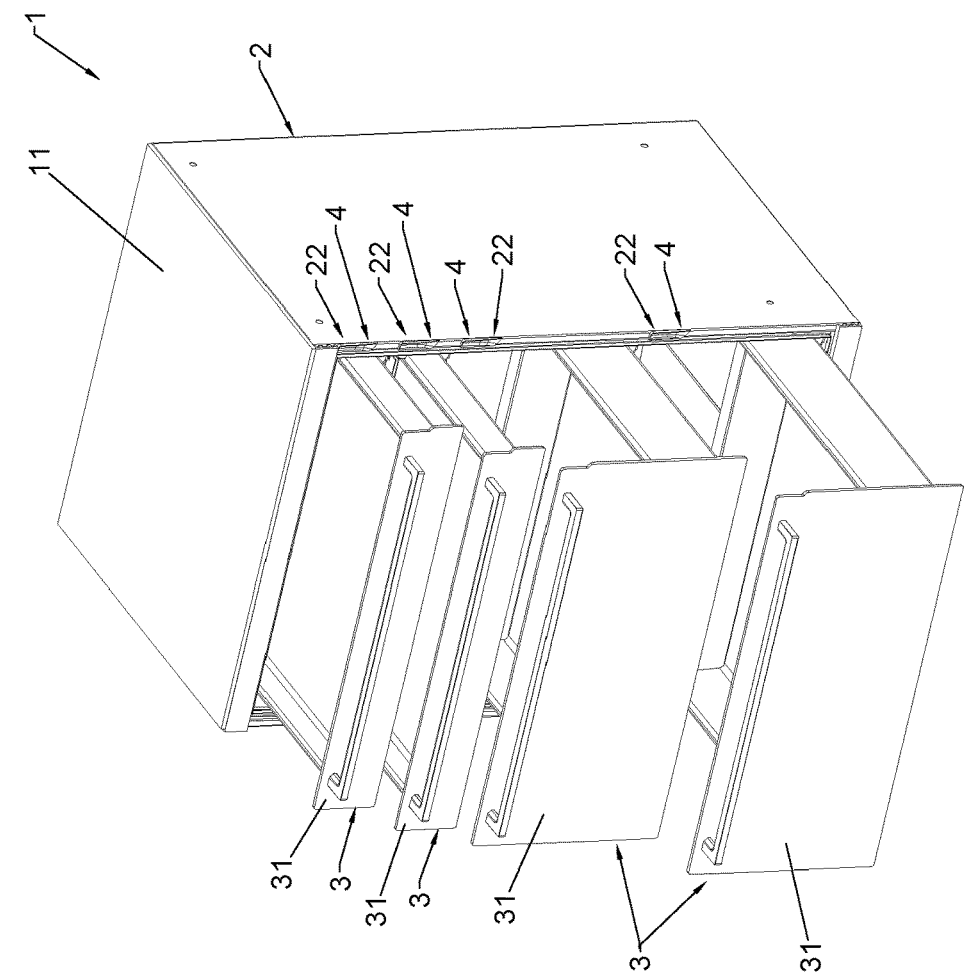
FIG. 4 shows an axonometric view of the chest of drawers of FIG. 1 with the drawers in the open position.

The chest of drawers according to a first embodiment of the invention is shown in FIG. 1 which is indicated as a whole with number 1.

This chest of drawers 1 can be used in homes, factories, shops, medical-surgical facilities and other places.

It is particularly suitable for use in medical-surgical facilities such as, for example, dental practices.

The chest of drawers 1 comprises a fixed structure 2 which defines at least one housing 21 which houses at least one movable drawer 3.

In particular, the fixed structure 2 has a substantially prismatic outline.

The fixed structure 2 comprises a pair of substantially vertical walls 12 facing each other and connected to each other by the interposition of an essentially horizontal upper top 11, as shown in FIG. 1.

Preferably but not necessarily, the fixed structure 2 comprises a lower base opposite the upper top 11.

This lower base is configured to be placed on a support surface, for example the floor, directly or through the use of support elements, commonly referred to as legs, installed under said lower base and in contact with the aforementioned support surface.

The fixed structure 2 and, if present, the lower base may be configured to be hung.

According to the first embodiment of the invention, the aforementioned housing 21 is defined in the internal volume of the aforementioned fixed structure 2 and is laterally delimited by the pair of vertical walls 12, by the upper top 11 and, if present, by the lower base, as shown in the Figures.

Figure 3:
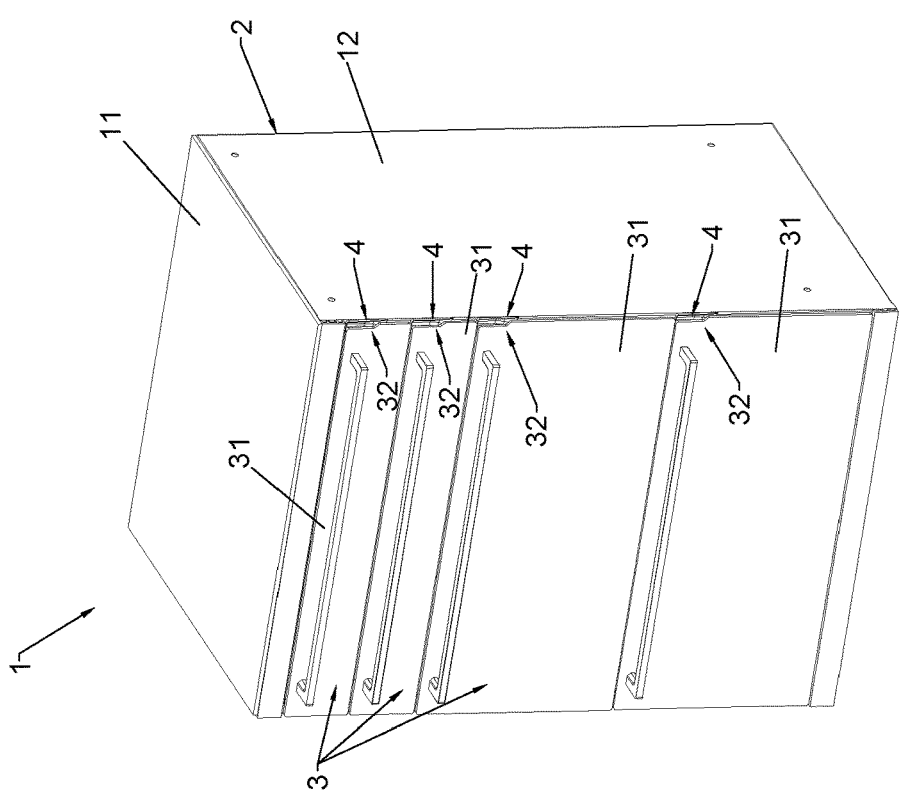
FIG. 3 shows an axonometric view of the chest of drawers of FIG. 1 with the drawers in the closed position.

Returning to the first embodiment of the invention, the drawer 3 is configured to have, with respect to the fixed structure 2, a closed position, shown in FIGS. 1 and 3, in which the drawer 3 is completely contained within the space of the housing 21.

The drawer 3 is also configured to have, with respect to the fixed structure 2, an open position, shown in FIG. 4, in which at least part of the drawer 3 protrudes outside the space of the housing 21.

The movement between the closed position and the open position, and vice versa, preferably takes place by sliding and more preferably by means of mechanical sliding elements whether automatic or manual.

By way of a non-limiting example, the mechanical sliding elements may comprise one or more slide guides, placed between the housing 21 and the drawer 3, and slide members associated with the drawer 3 suitable to slide over the aforementioned slide guides and thus move the drawer 3 with respect to the housing 21.

According to the first embodiment of the invention, the drawer 3, with its front side 31, can be made of any known material suited to be used in chests of drawers.

Preferably, at least the front side 31 of the aforementioned drawer 3 is opaque.

More preferably, at least the front side 31 of the aforementioned drawer 3 is not transparent.

According to the first embodiment of the invention, the fixed structure 2 comprises limit stops 15 (FIG. 2) for the drawer 3 defined laterally to the structure itself and projecting towards the inside of the housing 21.

These limit stops 15 are configured in such a way as to limit the movement, preferably the sliding, of the drawer 3 towards the inside of the housing 21 once the aforementioned drawer 3 reaches the closed position.

Preferably, these limit stops 15 are installed at the level of at least one vertical wall 12 of the pair of vertical walls 12 of the fixed structure 2, facing the front side 31, in particular facing the surface of the front side 31 of the drawer 3 which faces the inside of the housing 21 of the fixed structure 2.

Operationally, when the drawer 3 is in the closed position, it is in contact with these limit stops 15. In particular, the front side 31 of the drawer 3 is the part of the drawer that comes into contact with these limit stops 15 when the drawer 3 itself is in the closed position.

According to the first embodiment of the invention, the chest of drawers 1 comprises a first identification element 4 visible from the outside of the fixed structure 2.

Advantageously, this first identification element 4 is configured to provide information regarding the contents of the drawer 3 so that the healthcare professional can easily and quickly identify the contents of the drawer 3 from the outside and thus without having to open the drawer 3.

According to the first embodiment of the invention, the first identification element 4 is connected to the fixed structure 2 of the chest of drawers 1 so as to be visible from the outside of the latter.

According to alternative embodiments of the invention, this first identification element 4 may be connected to the drawer 3, provided that it is connected to a part of the drawer that is visible from the outside of the fixed structure 2 even when the drawer 3 is in the closed position, for example at the level of the front side 31.

According to the first embodiment of the invention, the first identification element 4 and the fixed structure 2 are provided with first and second coupling means, not shown in the figures, configured to mutually and removably connect the first identification element 4 and the fixed structure 2.

Preferably but not necessarily, said first and/or second coupling means comprise magnetic members.

In this way, the first identification element 4 is removably connected to the aforementioned fixed structure 2, advantageously enabling the users to remove it or replace it with another first identification element 4 as needed.

According to alternative embodiments of the invention, the first identification element 4 and the fixed structure 2 may be solidly connected to each other.

According to the first embodiment of the invention, the aforementioned first identification element 4 is monochromatic.

Advantageously, the use of a predefined color enables users to associate said predefined color with a specific category of instruments, or a type of material, or anything else, with no need to specifically write the list of said instruments, materials etc.

The drawer 3 will then contain the tools or materials or any other item pertaining to the category defined by the predefined color of the first identification element 4 corresponding to that specific drawer 3.

According to the first embodiment of the invention, the chest of drawers 1 comprises a plurality of drawers 3 and a plurality of first identification elements 4, each of which provides information about the contents of one of these drawers 3.

Preferably, each first identification element 4 has a different color from the color of the other first identification elements 4.

According to variant embodiments of the invention, two or more first identification elements 4 may have the same color.

Returning to the first embodiment of the invention, the first identification element 4 is placed at the level of an area 22 of the fixed structure 2 defined inside said housing 21, as shown in FIG. 4.

In particular, this area 22 is defined on the fixed structure 2 so as to be turned towards the surface of the front side 31 of the drawer 3 facing the inside of the housing 21.

Preferably but not necessarily, this area 22 is defined substantially at the level of at least one wall 12 of the pair of vertical walls 12 of the aforementioned fixed structure 2.

Also preferably, this area 22 is defined at the level of the limit stops described above.

Advantageously, the positioning of the first identification element 4 at the level of an area 22 of the fixed structure 2 defined inside the housing 21 enables the drawer 3 to be moved to open or close it without having to touch said first identification element 4, as occurs with the chests of drawers of the prior art in which this identification element is represented by the drawer front side itself or by adhesive labels glued on the front side.

The deterioration of this first identification element 4 upon use as a result of being touched is thus advantageously reduced.

Further advantageously, this arrangement of the first identification element 4 in the area 22 enables the order of the drawers 3 of the chest of drawers 1 to be freely modified or to replace a damaged drawer 3 with a new one, without having to modify or replace the corresponding identification element 4.

The front 31 of the drawer 3 is also provided with a portion 32 suitably shaped so as to enable this area 22 to be viewed from the outside and therefore the first identification element 4 placed in this area 22 can be seen from the outside.

Advantageously, this portion 32 is shaped in such a way as to enable the area 22 to be viewed even when the drawer 3 is in the closed position.

Figure 5:
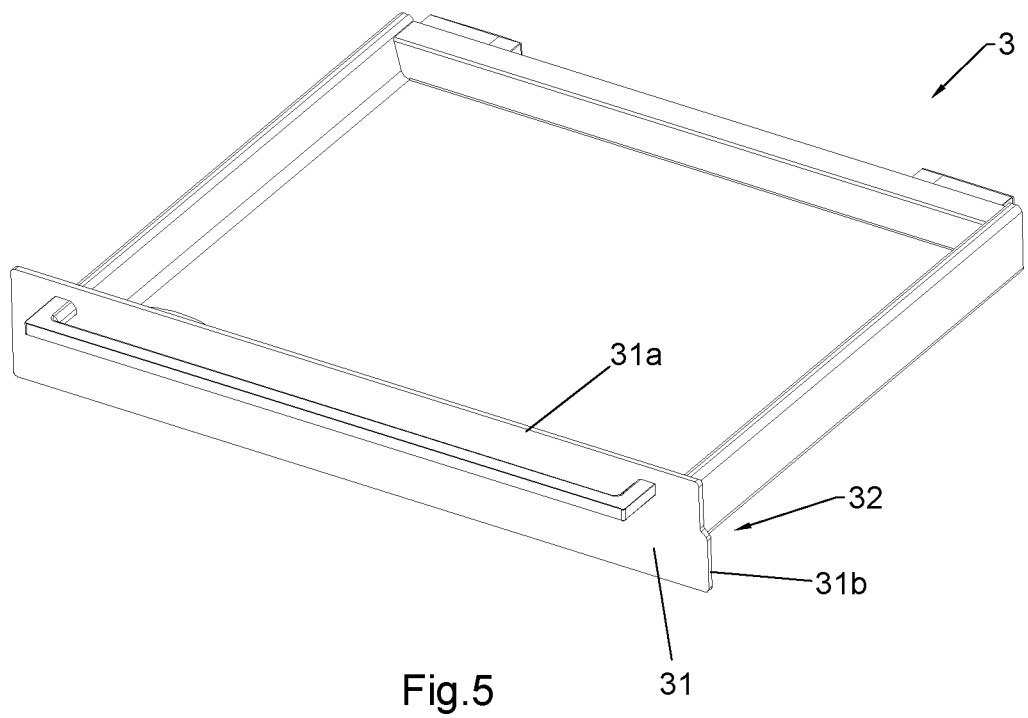
FIG. 5 shows an axonometric view of the drawer of the chest of drawers according to the first embodiment of the invention.

According to the first embodiment of the invention, the portion 32 is shaped with an open profile facing outwards and involves at least a portion of two perimeter edges 31a, 31b of the front side 31 which intersect each other, as shown in FIG. 5.

Figure 6:
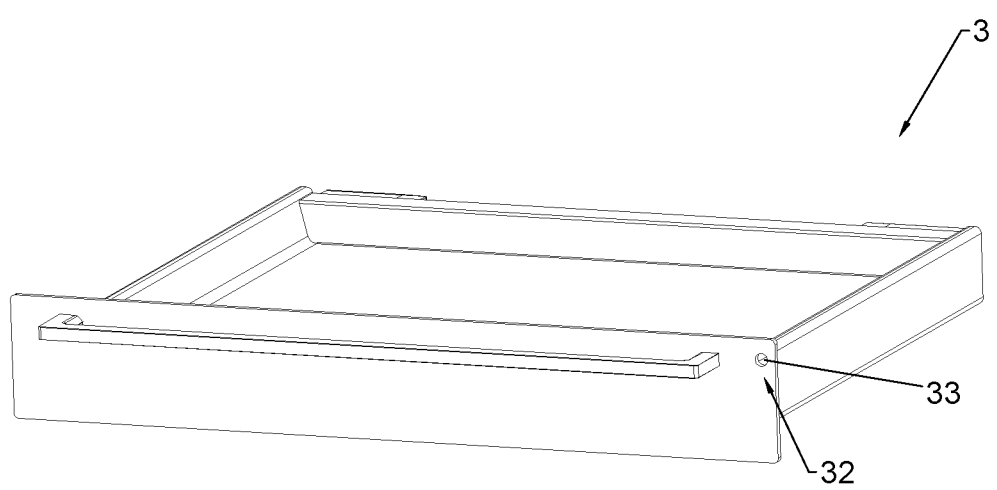
FIG. 6 shows an axonometric view of an alternative embodiment of the drawer of FIG. 5.

According to an alternative embodiment of the drawer 3 of the invention, shown in FIG. 6, the front side 31 provides for the presence of one or more through holes 33 at the level of the portion 32.

The area 22 and the first identification element 4 placed on it are visible from the outside of the fixed structure 2 through said one or more through holes 33, even when the drawer 3 is in the closed position.

Said one or more through holes 33 can have any shape, so as to advantageously provide a plurality of aesthetic combinations for the chest of drawers 1 according to the needs and the environment in which said chest of drawers will be used.

Figure 7:
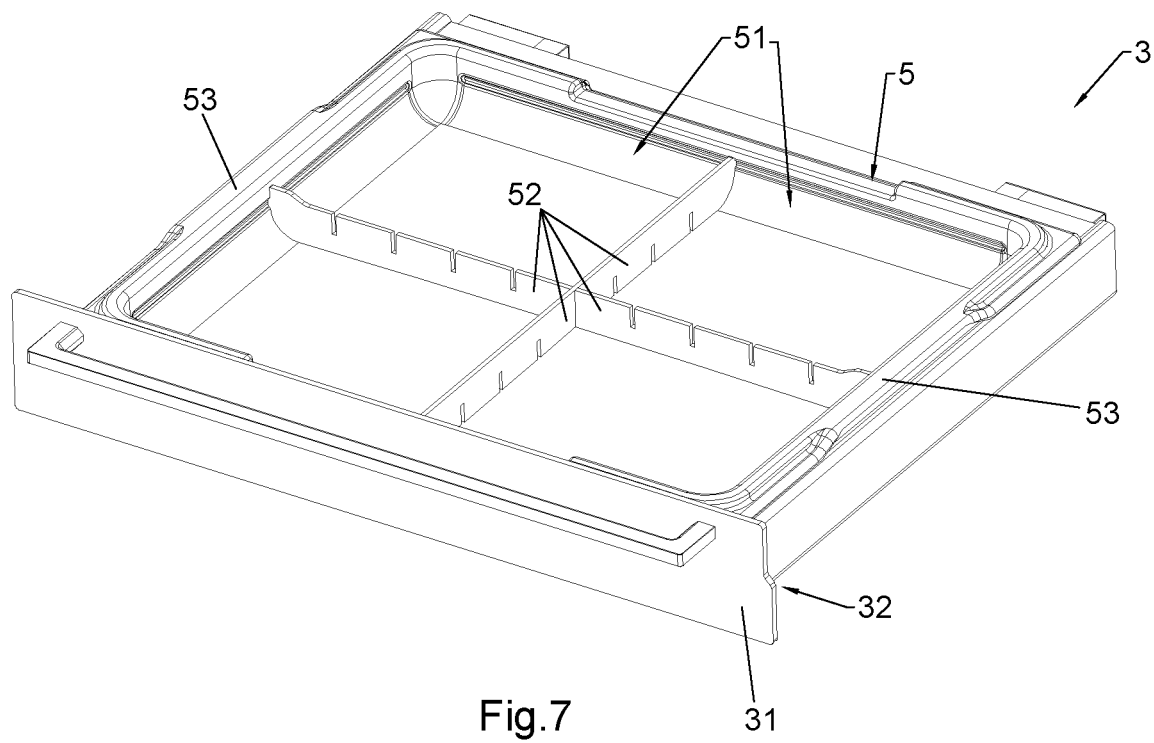
FIG. 7 shows an axonometric view of the drawer of FIG. 5 equipped with the container for instruments and/or materials housed therein.
Figure 8:
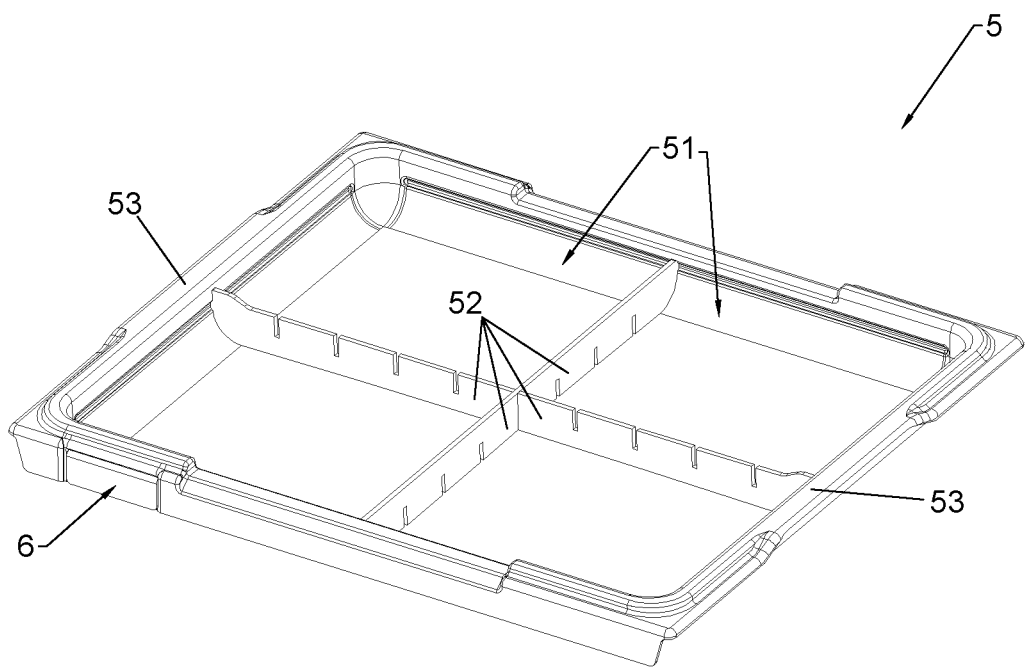
FIG. 8 shows an axonometric view of the container for instruments and/or materials shown in FIG. 7.

According to the first embodiment of the invention, the chest of drawers 1 further comprises a container 5 shown in FIGS. 7 and 8.

The container 5 is of a known type and intended to contain instruments, materials or any other instrumentation.

It preferably has a prismatic shape.

Also preferably, in this container 5 there are a plurality of compartments 51 created by a plurality of partitions 52 projecting from the bottom of the container 5 in a substantially vertical direction. Each compartment 51 is configured to contain one or more of the aforementioned tools, materials, etc.

As can be seen in particular from FIG. 7, this container 5 is removably housed inside the drawer 3.

To facilitate the separation of the container 5 from the inside of the drawer 3, it comprises one or more handles 53.

These handles 53 may have, by way of example, a loop or ring shape, and are arranged at the level of the lateral edges of the container 5.

Furthermore, they can be an integral part of the container 5, or they can be associated with it by means of suitable connection means.

Operationally, the handles 53 are gripped by the user to separate the container 5 from the inside of the drawer 3.

According to the first embodiment of the invention, the container 5 comprises a second identification element 6 removably coupled to the container 5 and configured to provide information regarding the contents of the drawer 3.

Preferably, the second identification element 6 is arranged at the edge of the container 5.

This second identification element 6 is also preferably monochromatic, so as to provide the advantages already mentioned above for the first identification element 4.

Advantageously, according to the first embodiment of the invention, the first identification element 4 and the second identification element 6 have the same color.

This characteristic enables the container 5 containing tools, materials, etc. to be unequivocally associated with the corresponding drawer 3.

This color matching between the first and the second identification element is particularly advantageous when the container 5 is separated from the drawer 3 and must subsequently be repositioned inside it.

According to alternative embodiments of the invention, the second identification element 6 may not have the same color as the first identification element 4, or the second identification element 6 may not be present.

According to the first embodiment of the invention, this second identification element 6 and the container 5 are also provided with first and second coupling means, not shown in the figures, configured to mutually and removably connect the second identification element 6 and the container 5.

Preferably but not necessarily, said first and/or second coupling means comprise magnetic members.

In this way, the second identification element 6 is removably connected to the container 5, advantageously enabling the user to remove it or replace it with another second identification element 6 depending on the needs.

Another aspect of the present invention relates to a method for identifying the contents of a drawer in a chest of drawers.

The aforementioned method preferably makes use of the chest of drawers 1 according to the first embodiment of the invention, including the alternative embodiments.

According to this method, the first identification element 4 is arranged on said chest of drawers 1 so that it is visible from the outside of the fixed structure 2.

As noted, the first identification element 4 is configured to provide information regarding the contents of the drawer 3 so that the user is able to know the contents of the drawer 3 without needing to open the drawer in question.

In particular, the aforementioned method provides for the placement of the first identification element 4 at the level of the area 22 of the fixed structure 2 defined inside the housing 21 and to shape the portion 32 of the front side 31 so as to enable this area 22 and the first identification element 4 to be viewed from the outside even when the drawer 3 is in the closed position.

Preferably, the method provides for shaping the portion 32 according to an open profile facing outwards and affecting at least one portion of the two perimeter edges 31a, 31b of the front side 31 which are incident to each other.

According to alternative embodiments of the method of the invention, the front side 31 may be shaped at the level of the portion 32 so as to create one or more through holes 33 in order to enable the area 22 and therefore the first identification element 4 to be viewed.

It is specified that, according to the method of the invention, when the chest of drawers 1 has a plurality of drawers 3 a plurality of first identification elements 4 is arranged on the chest of drawers 1, each of which provides information about the contents of one or more of the drawers of the plurality of drawers 3.

Preferably, the method of the invention provides for placing the first identification element 4 at the level of the limit stops of the aforementioned drawer 3.

These limit stops have already been previously described with reference to the chest of drawers 1 of the invention. Concisely, they are located on the fixed structure 2 projecting towards the inside of the housing 21 and are configured to stop the movement of the drawer 3 towards the inside of the housing 21 when the drawer 3 reaches its closed position.

It is clear that, in this case, the area 22 is defined at the level of these limit stops.

The method of the invention further provides for the removable coupling of the container 5 of the drawer 3 to a second identification element 6 intended to provide information regarding the contents of the drawer itself.

This second identification element 6 is preferably placed at the edge of the container 5, more preferably at the upper edge of the container 5.

Advantageously, the second identification element 6 of the container 5 is monochromatic and, preferably, has the same color as the first identification element 4 which provides information on the drawer 3 where the aforementioned container 5 is housed, achieving the previously mentioned advantages.

According to variant embodiments of the method of the invention, said operation of arranging the second identification element 6 may be omitted.

According to the above, therefore, the chest of drawers and the method of the invention achieve all the intended objects.

In particular, thanks to the first identification element it is possible to quickly identify the contents of each drawer present in the chest of drawers of the invention.

In addition, the particular configuration of the first and second identification element allows the identification of the drawer contents to be easily adaptable and modifiable by the user.

Last but not least, the particular shape of the drawer of the chest of drawers of the invention enables the contents of the drawer to be identified from the outside, without the need to open the drawer itself.

The invention claimed is:

1. A chest of drawers comprising:
   a fixed structure which defines at least one housing, said housing hosting at least one movable drawer;
   said at least one movable drawer configured to have a closed position with respect to said fixed structure in which said at least one movable drawer is completely contained inside said housing and an open position in which at least part of said at least one movable drawer protrudes outside said housing;
   a first identification element visible from the outside of said fixed structure, said first identification element being configured to provide information regarding the contents of said at least one movable drawer;
   wherein said at least one movable drawer comprises a front side provided with a portion suitably shaped so as to enable at least one area of said fixed structure defined inside said housing to be viewed from the outside, even when said at least one movable drawer is in said closed position, said first identification element being placed at a level of said at least one area of said fixed structure, wherein:
   said front side at a level of said portion provides a through hole; or
   said portion is shaped with an open profile facing outwards and includes at least one portion of two perimeter edges of said front side which are incident to each other; wherein said first identification element is magnetically coupled to said fixed structure.

2. The chest of drawers according to claim 1, wherein said fixed structure comprises a pair of substantially vertical walls facing each other and connected to each other by the interposition of an essentially horizontal upper top.

3. The chest of drawers according to claim 1, wherein said first identification element is monochromatic.

4. The chest of drawers according to claim 1, wherein said fixed structure comprises limit stops for said at least one movable drawer configured to stop the movement of said at least one movable drawer towards the inside of said housing when said at least one movable drawer reaches said closed position, said limit stops being located on said fixed structure projecting towards the inside of said housing, said area being defined at a level of said limit stops.

5. The chest of drawers according to claim 1, further comprising a container removably housed inside said at least one movable drawer, said container comprising a second identification element removably coupled to said container and configured to provide information regarding the contents of said at least one movable drawer.

6. The chest of drawers according to claim 5, wherein said first identification element and said second identification element have the same color.

7. The chest of drawers according to claim 5, wherein said container comprises one or more handles to facilitate the separation of said container from the inside of said at least one movable drawer.

8. A method for identifying the contents of a drawer in a chest of drawers, said chest of drawers comprising a fixed structure which defines at least one housing hosting at least one moveable drawer; said at least one movable drawer being configured to have a closed position with respect to said fixed structure in which said at least one movable drawer is completely contained inside said housing and an open position in which at least part of said at least one movable drawer protrudes outside said housing; said method providing for the placement of a first identification element on said fixed structure, the element being visible from the outside of said fixed structure; said first identification element being configured to provide information regarding the contents of said at least one movable drawer; a portion of the front side of said at least one movable drawer being shaped so as to allow at least one area of said fixed structure defined inside said housing to be viewed from the outside, even when said at least one movable drawer is in the closed position, said method providing for the placement of said first identification element at a level of said at least one area of said fixed structure;
   wherein:
   said front side at a level of said portion provides a through hole; or
   said portion is shaped with an open profile facing outwards and includes at least one portion of two perimeter edges of said front side which are incident to each other;
   said method comprising:
   moving said at least one movable drawer to said open position;
   placing said first identification element at the level of said at least one area of said fixed structure; and moving said at least one movable drawer to said closed position.

9. The method according to claim 8, wherein said first identification element is monochromatic.

10. The method according to claim 8, wherein said fixed structure comprises a pair of substantially vertical walls facing each other and connected to each other by the interposition of an essentially horizontal upper top.

11. The method according to claim 8, wherein said first identification element is placed at a level of limit stops of said at least one movable drawer; said limit stops being defined on said fixed structure projecting towards the inside of said housing and being configured to stop the movement of said at least one movable drawer towards the inside of said housing when said at least one movable drawer reaches said closed position, said area being defined at the level of said limit stops.

\* \* \* \* \*